(12) United States Patent
Kochhar et al.

(10) Patent No.: US 7,176,348 B2
(45) Date of Patent: Feb. 13, 2007

(54) COCOA POLYPEPTIDES AND THEIR USE IN THE PRODUCTION OF COCOA AND CHOCOLATE FLAVOR

(75) Inventors: Sunil Kochhar, Savigny (CH); Carl Erik Hansen, Epalinges (CH); Marcel Alexandre Juillerat, Lausanne 26 (CH)

(73) Assignee: Nestec S.A., Vevey (CH)

( * ) Notice: Subject to any disclaimer, the term of this patent is extended or adjusted under 35 U.S.C. 154(b) by 273 days.

(21) Appl. No.: 10/691,590

(22) Filed: Oct. 24, 2003

(65) Prior Publication Data

US 2004/0172683 A1 Sep. 2, 2004

Related U.S. Application Data

(63) Continuation of application No. PCT/EP02/04258, filed on Apr. 17, 2002.

(30) Foreign Application Priority Data

Apr. 25, 2001 (EP) .................................. 01110251

(51) Int. Cl.
*C12N 15/82* (2006.01)
*C07H 21/04* (2006.01)
*A01H 5/00* (2006.01)

(52) U.S. Cl. .................. 800/278; 435/468; 435/320.1; 435/419; 536/23.6

(58) Field of Classification Search ..................... None
See application file for complete search history.

(56) References Cited

U.S. PATENT DOCUMENTS 5,770,433 A * 6/1998 Spencer et al. ........ 435/252.33

FOREIGN PATENT DOCUMENTS

| WO | WO91/06570 | 5/1991 |
| WO | WO91/19800 | 12/1991 |
| WO | WO91/19801 | 12/1991 |
| WO | WO96/38472 | 12/1996 |
| WO | WO98/27805 | 7/1998 |

OTHER PUBLICATIONS

Roedel W, Habisch D, and Ruttloff H. Formation of cocoa flavor by the Maillard reaction. (1988) Charact., Prod. Appl. Food Flavours, pp. 301-309.*
Kochhar S, Gartenmann K, Guilloteau M, and McCarthy J. Isolation and Characterization of 2S Cocoa Seed Albumin Storage Polypeptide and the Corresponding DNA. (2001) J. Agric. Food Chem., vol. 49, pp. 4470-4477.*
Hansen CE, Manez A, Burri C, and Bousbaine A. Comparison of enzyme activities involved in flavour precursor formation in unfermented beans of different cocoa genotypes. (2000) J. Sci. Food Agric., vol. 80, pp. 1193-1198.*
Yavuz, M.O. et al., "Expression of the major bean proteins from *Theobroma cacao* (cocoa) in the yeasts *Hansenula polymorpha* and *Saccharomyces cerevisiae*", Journal of Biotechnology, vol. 46, pp. 43-54 (1996).
Voigt, J. et al., "Cocoa-specific aroma precursors are generated by proteolytic digestion of the vicilin-like globulin of cocoa seeds", Food Chemistry, vol. 50, pp. 177-184 (1994).
Voigt, J. et al., "*In vitro* studies on the proteolytic formation of the characteristic aroma precursors of fermented cocoa seeds: The significance of endoprotease specificity", Food Chemistry, vol. 51, pp. 7-14 (1994).

* cited by examiner

*Primary Examiner*—Ashwin D. Mehta
*Assistant Examiner*—Cathy Kingdon Worley
(74) *Attorney, Agent, or Firm*—Bell, Boyd & Lloyd LLP

(57) ABSTRACT

The present invention pertains to novel cocoa polypeptides having a molecular weight of about 10 and 14 kDa and being derived from a 69 kDa precursor. In particular, the present invention relates to the production of the polypeptides via recombinant means and the use of the polypeptides or fragments thereof for the production of cocoa/chocolate flavor.

8 Claims, 2 Drawing Sheets

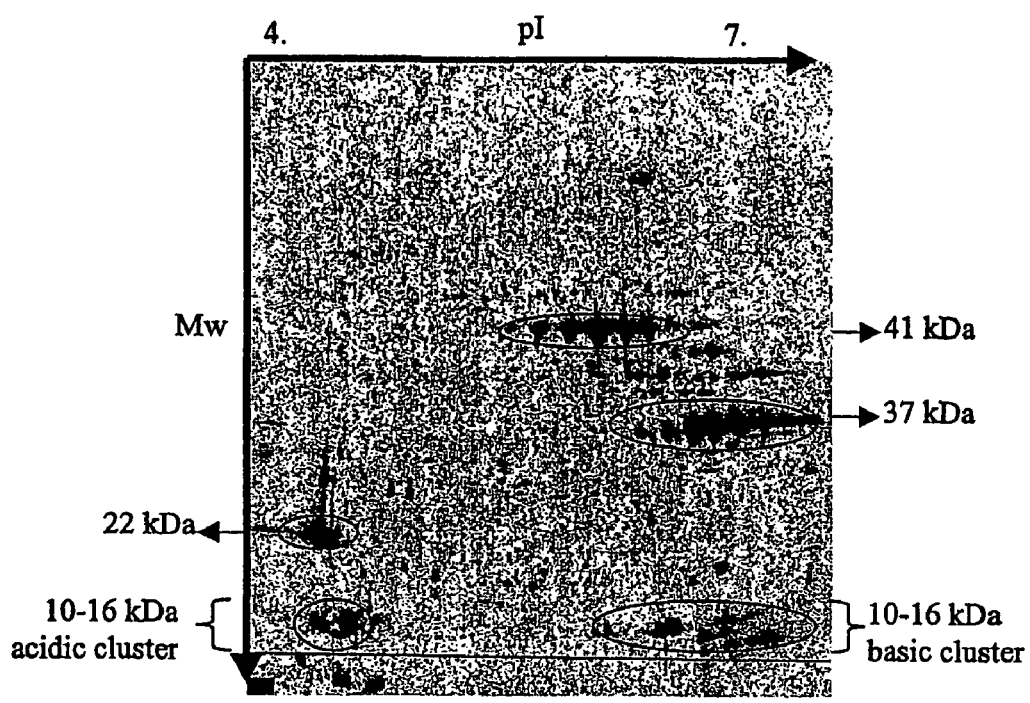
Fig. 1: Two-dimensional SDS-PAGE pattern of unfermented cocoa. Protein spots are visulized by silver staining.

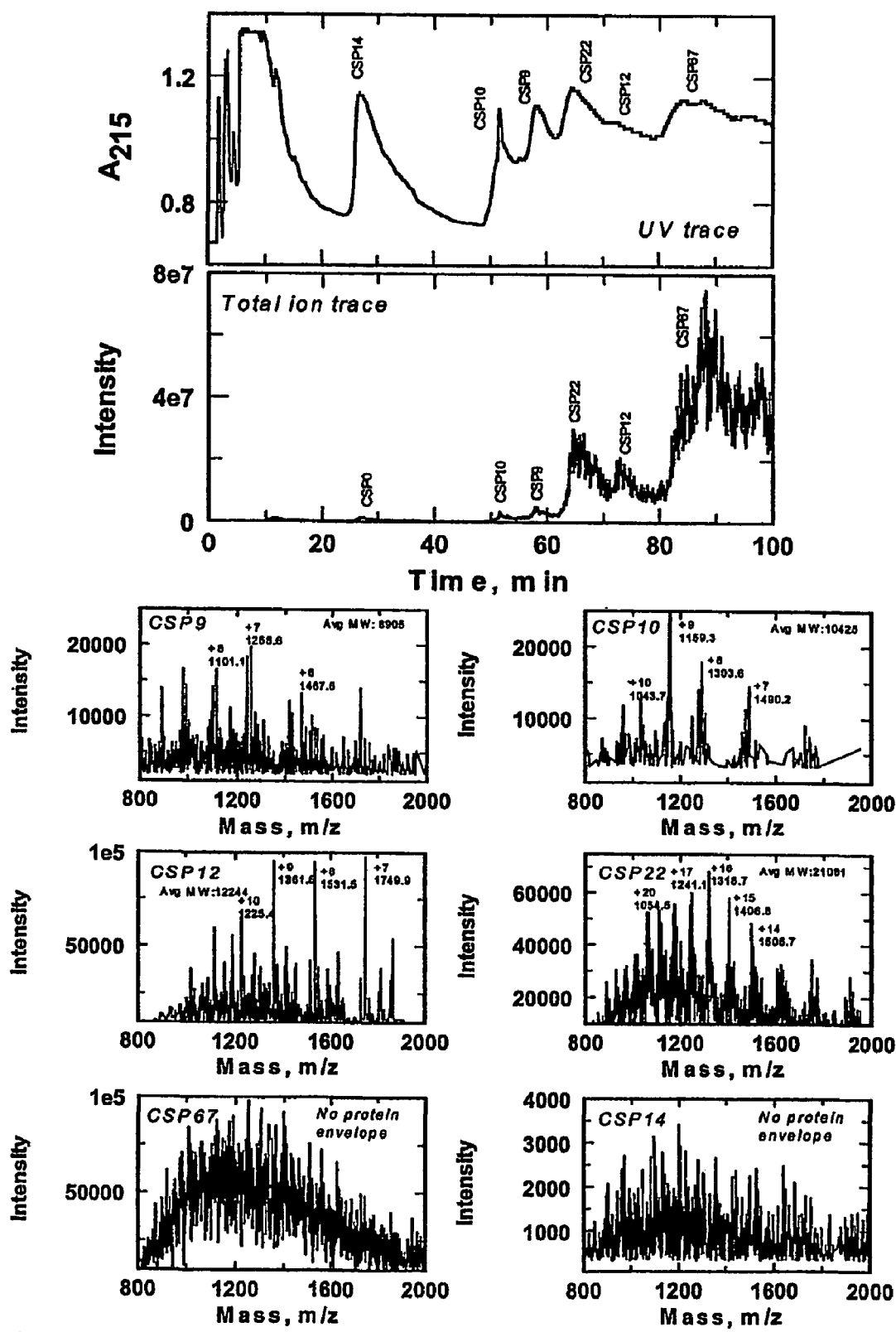
Fig2. LC/MS data for molecular mass determination of cocoa polypeptides

SEQUENCE LISTING

<160> NUMBER OF SEQ ID NOS: 4

<210> SEQ ID NO 1
<211> LENGTH: 89
<212> TYPE: PRT
<213> ORGANISM: Theobroma cacao

<400> SEQUENCE: 1

```
Arg Arg Glu Gln Glu Glu Glu Ser Glu Glu Glu Thr Phe Gly Glu Phe
1               5                   10                  15

Gln Gln Val Lys Ala Pro Leu Ser Pro Gly Asp Val Phe Val Ala Pro
            20                  25                  30

Ala Gly His Ala Val Thr Phe Phe Ala Ser Lys Asp Gln Pro Leu Asn
        35                  40                  45

Ala Val Ala Phe Gly Leu Asn Ala Gln Asn Asn Gln Arg Ile Phe Leu
    50                  55                  60

Ala Gly Arg Pro Phe Phe Leu Asn His Lys Gln Asn Thr Asn Val Ile
65                  70                  75                  80

Lys Phe Thr Val Lys Ala Ser Ala Tyr
                85
```

<210> SEQ ID NO 2
<211> LENGTH: 101
<212> TYPE: PRT
<213> ORGANISM: Theobroma cacao

<400> SEQUENCE: 2

```
Gly Arg Lys Gln Tyr Glu Arg Asp Pro Arg Gln Gln Tyr Glu Gln Cys
1               5                   10                  15

Gln Arg Arg Cys Glu Ser Glu Ala Thr Glu Glu Arg Glu Gln Glu Gln
            20                  25                  30

Cys Glu Gln Arg Cys Glu Arg Glu Tyr Lys Glu Gln Gln Arg Gln Gln
        35                  40                  45

Glu Glu Glu Leu Gln Arg Gln Tyr Gln Gln Cys Gln Gly Arg Cys Gln
    50                  55                  60

Glu Gln Gln Gln Gly Gln Arg Glu Gln Gln Gln Cys Gln Arg Lys Cys
65                  70                  75                  80
```

```
Trp Glu Gln Tyr Lys Glu Gln Glu Arg Gly Glu His Glu Asn Tyr His
                85                  90                  95

Asn His Lys Lys Asn
            100

<210> SEQ ID NO 3
<211> LENGTH: 26
<212> TYPE: PRT
<213> ORGANISM: Theobroma cacao
<220> FEATURE:
<221> NAME/KEY: VARIANT
<222> LOCATION: (17)..(17)
<223> OTHER INFORMATION: Xaa can be any amino acid
<220> FEATURE:
<221> NAME/KEY: VARIANT
<222> LOCATION: (20)..(20)
<223> OTHER INFORMATION: Xaa can be any amino acid
<220> FEATURE:
<221> NAME/KEY: VARIANT
<222> LOCATION: (24)..(24)
<223> OTHER INFORMATION: Xaa can be any amino acid

<400> SEQUENCE: 3

Arg Arg Glu Gln Glu Glu Glu Ser Glu Glu Glu Thr Phe Gly Glu Phe
1               5                   10                  15

Xaa Gln Val Xaa Ala Pro Leu Xaa Pro Gly
            20                  25

<210> SEQ ID NO 4
<211> LENGTH: 10
<212> TYPE: PRT
<213> ORGANISM: Theobroma cacao

<400> SEQUENCE: 4

Gly Arg Lys Gln Tyr Glu Arg Asp Pro Arg
1               5                   10
```

US 7,176,348 B2

COCOA POLYPEPTIDES AND THEIR USE IN THE PRODUCTION OF COCOA AND CHOCOLATE FLAVOR

CROSS-REFERENCE TO RELATED APPLICATIONS

This application is a continuation of International Application PCT/EP02/04258 filed Apr. 17, 2002, the content of which is expressly incorporated herein by reference thereto.

FIELD OF THE INVENTION

The present invention relates to novel cocoa polypeptides having a molecular weight of about 10 and 14 kDa. The newly identified peptides were first derived from a 69 kDa precursor. In particular, the present invention relates to the production of the polypeptides via recombinant means and the use of the polypeptides or fragments thereof for the production of cocoa/chocolate flavor.

BACKGROUND OF THE INVENTION

The traditional processing of coca beans to generate cocoa flavor requires two steps—a fermentation step, which includes air-drying of the fermented material, and a roasting step.

During fermentation the pulp surrounding the beans is degraded by micro-organisms and the sugars contained in the pulp are mainly transformed to acids. In the course of the fermentative process these acids slowly diffuse into the bean eventually causing an acidification of the cellular material. Furthermore, during fermentation peptides of different sizes are generated as well as high levels of hydrophobic free amino acids, which are mainly attributed to the activity of specific proteinases. This specific mixture of peptides and hydrophobic amino acids is thought to be the cocoa-specific flavor precursors.

Research to date has focused on the different proteolytic enzymes involved in these reactions. A number of different types of enzymes, such as an aspartic endoproteinase, a cysteine endoproteinase or a carboxypeptidase have been found to participate in these degradative reactions leading to the formation of the cocoa flavor peptide/amino acid precursor pool.

During the second step of cocoa flavor production—the roasting step—the oligopeptides and amino acids generated during the fermentation stage are subjected to a Maillard reaction in the presence of reducing sugars in the mixture, yielding substances thought to be responsible for the typical cocoa flavor.

There have been attempts to artificially produce cocoa flavor in the past, such as, by subjecting acetone dried powder prepared from unfermented ripe cocoa beans to autolysis at a pH of 5.2 followed by roasting in the presence of reducing sugars. It was taught that under these conditions preferentially free hydrophobic amino acids and hydrophilic peptides would be generated. The peptide pattern obtained from this process was found to be similar to that of extracts from fermented cocoa beans.

Analysis of free amino acids revealed that Leu, Ala, Phe and Val were the predominant amino acids liberated in fermented beans or autolysis (Voigt et al., Food Chem. 49 (1994), 173–180). In contrast to these findings no cocoa-specific flavor could be detected when the above powder was subjected to autolysis at a pH of 3.5. Few free amino acids were found in the by product of the autolysis, but there were a large number of hydrophobic peptides formed.

Synthetic mixture of free amino acids whose composition resembles that found in fermented beans also have been found to not produce the cocoa flavor desired. These findings indicate that both the peptides and the amino acids are important in producing cocoa flavor (Voigt et al., Food Chem. 49 (1994), 173–180.

To date, little attention has been paid to the protein pool from which the peptide/amino acid flavor precursor pool is generated from, since cocoa proteins are often difficult to isolate. One of the major reasons is because that coca seeds contain a high amount of polyphenols and fat. Separating the polyphenols and fat traditionally requires the use of lipophilic organic liquids, such as acetone. The use of these liquids often result in the removal of lipophilic flavor precursors and active substances. Another reason is because of the poor solubilization of proteins purified with acetone, resulting in a poor recovery of the total proteins.

To date, four major proteins with an apparent molecular weight of 14.5, 21, 31 and 47 kDa, have been identified before fermentation in cocoa bens. These proteins are thought to give rise to the peptide/amino acid pool responsible for producing the cocoa flavor.

It is an object of the present invention to further elucidate and identify other protein responsible for producing the cocoa flavor in sufficient detail to eventually provide means for improving the preparation of cocoa flavor and cocoa flavor substitutes.

SUMMARY OF THE INVENTION

The present invention is directed to an isolated or synthesized cocoa polypeptide identified by SEQ ID NO:1, SEQ ID NO:2, or a fragment thereof comprising SEQ ID NO:3 or SEQ ID NO:4. These newly identified peptides have a molecular weight of about 10 and 14 kDa, respectively, and were originally derived from the 69 kDa cocoa bean precursor proteins.

Typically fragments of the SEQ ID NO:1 and SEQ ID NO:2 are obtained by enzymatic degradation, preferable using one or more of the following enzymes: aspartic endoproteinase, cysteine endoproteinase and carboxypeptidase. In one embodiment the enzymes used are derived from cocoa plants.

The present invention is also directed to an isolated or synthesized nucleotide sequence that encodes SEQ ID NO:1, SEQ ID NO:2 or fragments thereof. In those embodiments wherein the nucleotide sequence of the invention encodes a fragment of SEQ ID NO:1 and/or SEQ ID NO:2. The peptides encoded by these nucleotides preferably comprises SEQ ID NO:3 and/or SEQ ID NO:4.

The present invention encompasses recombinant cells, vectors, and cells comprising vectors containing one or more copies of the nucleotide sequence described above.

Typically the recombinant cell is a bacterial cell, a yeast cell, an insect cell, a mammalian cell or a plant cell. Preferably the cell is a plant cell and most preferably are part of a plant.

The present invention is further directed to a method of producing cocoa or chocolate flavor comprising isolating, synthesising or producing a polypeptide of the invention. In one embodiment, the method further comprises reacting such a peptide with a reducing sugar.

In yet another embodiment of the invention, the newly identified peptides are used to enhance the cocoa or chocolate flavor of a composition. The method typically comprises supplementing a food composition with one or more of the peptides.

The method can further comprise subjecting the peptide to enzymatic degradation, preferably involving one or more of the following enzymes: aspartic endoproteinase, cysteine endoproteinase or carboxypeptidase, followed by reacting the fragments with reducing sugars.

Still further, the present invention also encompasses a method of producing cocoa beans with increased cocoa flavor proteins. The method typically comprises transforming a cocoa cell with one or more of the nucleotide sequences of the invention followed by generating at least one cocoa plant from the transformed cell. Preferably the transformed cell comprises at least 40 copies of the nucleotide sequence.

BRIEF DESCRIPTION OF THE DRAWINGS

FIG. 1 shows photograph of a two-dimensional SDS-PAGE proteins isolated from unfermented cocoa beans;

FIG. 2 shows the result of a LC_ESI-MS analysis of a GndHCL extract of unfermented cocoa beans.

DETAILED DESCRIPTION OF THE PREFERRED EMBODIMENTS

During the studies leading to the invention the present inventors have designed novel methods for an improved isolation of cocoa proteins by using denaturing agents, such as e.g. SDS (1%), urea or GndHCl, which resulted in an about 3-fold increase in solubility of proteins as compared to conventional methods. In particular, the use of 6 M GndHCl provided good results. GndHCl showed up to be easily removable by RP-HPLC and no reaction with the proteins occurred. Moreover, it could also be shown that even crude bean powder, after subjection to a treatment with a solubilization buffer including a denaturing agent could be successfully analysed, which made no special care necessary to remove polyphenols.

During the above-described studies directed to provide a better total recovery of cocoa proteins, the inventors ran a crude coca bean powder on a two-dimension SDS-PAGE gel, whereby a cluster of several polypeptides exhibiting a molecular weight of about 9–16 kDa, were detected. The polypeptides contained in the acidic cluster was further isolated by making use of RP-HPLC.

Finally two polypeptides were isolated having a molecular weight of about 10 and about 14 kDa. These polypeptides were N-terminally sequenced and are identified as SEQ ID NO:3 (10 kDa protein; AA residues 1–26 of SEQ ID NO:1) and SEQ ID NO:4 (14 kDa protein; AA residues 1–10 of SEQ ID NO:2), respectively.

Upon comparison with known protein sequences it was shown that these polypeptides were derived from the 69 kDa precursor protein. Upon processing the 69 kDa cocoa beans precursor, it gave rise to the above mentioned 47 and 31 kDa proteins and also to the newly identified 10 and 14 kDa proteins, also representing part of the protein/peptide pool of cocoa beans.

The present invention is directed to an isolated or synthesized cocoa polypeptide identified by SEQ ID NO:1, SEQ ID NO:2. According to another embodiment the present invention, the polypeptides are subjected to enzymatic degradation, preferably with aspartic endoproteinases, cystein endoproteinases and/or carboxypeptidases. In this embodiment it is preferable that the fragments comprise SEQ ID NO:3 or SEQ ID NO:4.

According to yet another embodiment the invention the polypeptides obtainable by the enzymatic degradation are subsequently reacted with reducing sugars.

The present invention also provides for a recombinant nucleotide encoding the polypeptides of the invention, preferably a nucleotide sequence encoding at least one of the new polypeptides or fragments thereof. Such nucleotides may be easily derived from the given polypeptide sequence by translating the amino acid according to the genetic code into corresponding triplets. Such a nucleotide sequence may well be expressed in a suitable cell by means well known in the art, such as e.g. in a bacterial cell, e.g. in *E. coli*, or in yeast, insect cells, mammalian or plant cells.

To this end, a nucleotide sequence encoding a polypeptide of the present invention is inserted into a suitable vehicle, such as an expression vector, and is incorporated into a cell of choice. With respect to plant cells, the nucleotides encoding the polypeptides of the present invention may also be incorporated into any of the plant cell's chromosome by using e.g. the phenomenon of homologous recombination. In this respect, at least one copy, preferably more than 40 copies of a nucleotide sequence, encoding any of the present polypeptides may be present on the DNA sequence to be inserted into a plants cell's chromosome.

The present invention further encompasses the generation of plants comprising the recombinant cells. Preferably the transformed plant is a cocoa plant.

Furthermore, the invention provides for the use of the polypeptides for the manufacture of cocoa flavor. To this end it is conceived that the present polypeptides may be added to a fermentation mixture of cocoa beans, in order to provide a higher amount of the polypeptides for degradation. When using cocoa plants that have been modified by recombinant means and contain a high number of copies of nucleotide sequences encoding the polypeptides of the present invention, the plants will inherently contain a higher concentration of the polypeptides and eventually will result in the production of a stronger cocoa flavor after the processing.

EXAMPLES

These and other aspects of the present invention may be more fully understood with reference to the following non-limiting examples, which are merely illustrative of the preferred embodiments of the present invention, and are not to be construed as limiting the invention, the scope of which is defined by the appended claims.

The following examples illustrate the invention in a more detailed manner. It is, however, understood that the present invention is not limited to the examples but is rather embraced by the scope of the appended claims.

Example 1

Separation of Proteins
Preparation of Crude Cocoa Bean Powder
Unfermented cocoa beans were obtained from Ivory Coast and unless stated otherwise all studies were carried out using West African Amelonado cocoa beans. Dried cocoa beans were passed through a bean crusher, followed by a winnover to remove shells. The nibs were kept in a brown bottle at −20° C. Cocoa nibs were milled for few seconds in an universal mill. The nib powder was passed through 0.8-mm sieve and kept at 4° C.

Two-Dimensional SDS-PAGE Electrophoretic Analysis of Unfermented Cocoa Bean

Crude (unfermented) cocoa bean powder (100 mg) was dissolved in 1 ml of solubilization buffer [8 M urea, 3% (w/v) CHAPS, 2.8% (v/v) carrier ampholytes (ampholine pH range 4–6.5, 5–8, and 3–10 (2:4:1) and 10 mM DTT (dithiothreitol)]. The clear supernatant was subjected to first dimension of separation on an immobilized pH-gradient (IPG) from 4–7, and second dimension on a 10% T SDS-PAGE gel. Proteins were visualized by silver staining.

The resulting electrophoretic profile of proteins in a typical unfermented cocoa bean on a two-dimensional SDS-PAGE is shown in FIG. 1. The 47, 31 and 21 kDa proteins were represented by several subforms and in addition two distinct clusters (acidic and basic) were clearly identified in a molecular weight range of about 9–16 kDa. All of the protein spots could be shown to gradually disappear upon fermenation of beans.

A Tricine-SDS-PAGE of unfermented cocoa bean genotypes showed up that the clusters in the molecular weight region 9–16 kDa were present in all of the 21 different genotypes representing three cocoa groups, namely Criollo, Forastero and Trinitario.

The acidic cluster has been selected for further investigation.

Example 2

Isolation of Proteins having a Molecular Weight of about 9–16 kDa

Preparation of an GndHCl Extract of CAP

Cocoa nib powder (10 g) (supra) was suspended in 200 ml 80% (v/v) aequous acetone and stirred for 1 hr at 4° C. The resulting suspension was centrifuged at 15.000 rpm for 15 min at 4° C. The residue was extracted 5-times with 200 ml 80% (v/v) aequous acetone and followed by 3-times washing with 100% acetone. The resulting acetone powder was dried under reduced pressure.

Subsequently a GndHCl extract and a pyridine-ethylated GndHCl extract of CAP from unfermented cocoa beans was prepared. 1 g CAP was suspended with 10 ml GndHCl buffer (100 mM ammonium phosphate, 66.7 mM potassium hydroxide, 3 mM EDTA and 6 M GndHCl) and sonicated for 1 min. The suspension was cooled on ice for 15–30 min and centrifuged at 15000 rpm at 4° C. for 15 min. The clear supernatant was carefully removed. In order to obtain a pyridine-ethylated GndHCl extract, the CAP extract (2 ml) was sparged with argon and mixed with 50 µl of reducing solution (0.8 M DTT in 3 M tripotassium phosphate/3 mM EDTA). The solution was kept at room temperature in dark for 60 min. Pyridine-ethylation at cysteine residues of the reduced CAP was carried out by mixing vigorously 40 µl of 4-vinyl pyridine and further incubation for 30 min at room temperature (Lundell and Schreitmüller, Anal. Biochem. 266 (1999) 31–47). The reaction mixture was dialyzed against 500 ml of the extraction buffer for overnight at room temperature. The dialyzed sample was centrifuged and the clear supernatant passed through 0.22 µm filter disc and kept at 4° C. until analyzation.

LC-ESI-MS Analysis of the Reduced and Pyridylethylated GndHCl-Extract

A LC-ESI-MS analysis of the reduced and pyridylethylated extract was performed, as may be seen from FIG. 2. To this end, reduced and pyridylethylated GndHCl extracts of CAP were injected onto reverse phase HPLC columns [BIO-RAD® HRLC series 800 system; columns C4 and C8 from Aquapore RP butyl (7 µm, 4.6×220 mm), Aquapore RP 300 (7 µm, 4.6×220 mm), Perkin-Elmer; Spherisorb 80–5C8 (220×4 mm); Marchery Nagel and Vydac protein C4 (4.6× 220 mm)) pre-equilibrated with solvent A (0.1% v/v TFA in water) and eluted with a linear gradient of increasing concentration of solvent B (80% v/v acetonitrile and 0.1% v/v TFA): 0–15% B in 5 min, 15–27% B in 40 min, 27–35% B in 2 min, isocratic at 35% B for 3 min, 35–43% B in 25 min, 43–56% B in 50 min, 56–70% B in 5 min, 70–100% B in 10 min and isocratic at 100% B for 5 min].

Fractions containing proteins were found to elute at a retention time of about 41, 52, 68, 78 and 87 min, were of about $M_r$ 10,425 (marked as CSP10), 9,010 (marked as CSP9), 20,540 (marked as CSP22) and 12,500 (marked as CSP12), respectively, as can be seen in Table 1 and FIG. 6. In the case of proteins eluting at 41 min and 97 min, no molecular mass could be identified.

TABLE 1

| Retention time, min | Sample code | Average $M_r$ | Comments |
|---|---|---|---|
| 41.4 | CSP14 | Not detected | |
| 52.5 | CSP10 | 10,425 | |
| 67.7 | CSP9 | 9,010 | |
| 78.5 | CSP22 | 20,540 | Albumin CSP |
| 86.9 | CSP12 | 12,245 | |
| 97.3 | CSP67 | Not detected | Vicilin type CSP |
| 132.2 | CSPAgg | Not detected | |

Since the average Mw of the protein designated CSP14 could not be assigned with the above method, the peak fraction was dissolved in 500 µl of 25% solvent B (0.05% (v/v) TFA/80%, v/v ACN). For SDS-PAGE, a 10 µl aliquot was dried in a SPEEDVAC® low vacuum system and dissolved in 20 µl SDS-sample buffer and analyzed on gradient 10–20% T ready Tris-Tricine acrylamide gels using the miniprotean 3 system from BIO-RAD®. Protein bands were visualized by staining the gels in the staining solution [0.5% (w/v) Commassie Brilliant Blue R250 in 30% (v/v) methanol and 10% (v/v) acetic acid] for 1 hr followed by destaining [30% (v/v) methanol plus 10% (v/v) acetic acid] until bands were visible against the clear background (Graffin, Methods Enzymol. 182 (1990) 425–477). Accordingly it could be observed that CSP 14 corresponds to a protein having a molecular weight of about 14 kDa.

Purification/Collection by Repetitve RP-HPLC

Subsequently, the cocoa proteins, reduced and pyridine-ethylated were isolated/collected by repetitive injections and automatic fraction pooling and collection from the GndHCl extracts of unfermented CAP, as described above. The pooled fractions of each proteins were dried under reduced pressure and dissolved in 400 µl solvent A and rechromatographed [column Aquapore RP 300 (7 µm, 4.6×220 mm), solvent TFA/ACN system; injection volume 400 µl; detection at 215 nm; gradients: 1. FIG. 7a (CSP14) and FIG. 7b (CSP9): 0–15% B in 5 min, isocratic at 15% B for 5 min, 15–35% B in 60 min, 35–50% B in 10 min, 50–100% B in 5 min and isocratic at 100% B for 5 min; 2. FIG. 7c (CSP12): 0–35% B in 5 min, isocratic at 15% B for 5 min, 35–60% B in 60 min, 60–75% B in 10 min, 75–100% B in 10 min and isocratic at 100% B for 10 min;]. Fractions 1 ml each were automatically collected and those containing the peak fractions for each of CSP14 and CSP10 were pooled, dried and kept at −20° C. until used.

Example 3

Characterization of Purified Proteins

The purified cocoa seed proteins CSP10 and CSP14 were subjected to N-terminal amino acid sequencing by automated Edman degradation protein sequencer. The initial and repetitive yield of Edman cycle was between 80 to 90%. The results obtained are shown in table 2 below.

TABLE 2

| Protein | Initial amount, pmol | Initial yield, pmol | Sequence |
|---------|----------------------|---------------------|----------|
| CSP10 | 400 | 120 | RREQE EESEE ETFGE FXQVX APLXP G (SEQ ID NO:3) |
| CSP14 | 200 | 100 | GRKQY ERDPR (SEQ ID NO4) |

The above listed N-terminal sequence of CSP 10 and 14 has been found to be a part of the 67 kDa vicilin type cocoa storage protein (WO 91/19801, supra). Thus, both of CSP 10 and 14 are so far not identified fragments of the 67 kDa vicilin type cocoa storage protein produced during the normal processing of the protein in cacao beans. By aligning the 47 and 31 kDa proteins, known to be derived from the 67 kDa vicillin protein, to the protein the remaining sequence for the CSP 10 and 14 was derived, which yielded the sequences as identified by SEQ ID NO:1 and SEQ ID NO:2.

A calculation of the molecular weights of the amino acids contained in the polypeptides according to SEQ ID NO:1 and 2 confirmed the approximate molecular weights of the resulting polypeptides were about 10 and 14 kDa.

Consequently the peptides also seem to be excised during the normal processing of the 67 kDa protein and represent a part of the protein/polypeptide pool of cacao beans.

---

What is claimed is:

1. An isolated or synthesized polynucleotide consisting of a nucleotide sequence encoding the polypeptide of SEQ ID NO: 1 or SEQ ID NO:3.

2. A vector containing the polynucleotide of claim 1 operably linked to a promoter.

3. A non-human cell containing the vector of claim 2.

4. The cell according to claim 3, which is a bacterial cell, a yeast cell, an insect cell, a mammalian cell or a plant cell.

5. A plant containing the plant cell of claim 4.

6. The plant of claim 5, wherein the plant is a cocoa plant.

7. A method of producing cocoa beans with increased cocoa flavor peptides, the method comprising transforming a cocoa cell with the vector of claim 2 and generating at least one cocoa plant from the transformed cell, and producing cocoa beans from the transformed plant, wherein the beans express said polypeptide.

8. The method of claim 7, wherein the cell comprises at least 40 copies of the nucleotide sequence.

* * * * *